United States Patent
Regnier et al.

(10) Patent No.: US 11,197,997 B2
(45) Date of Patent: Dec. 14, 2021

(54) AUTONOMOUS IMPLANTABLE CARDIAC CAPSULE WITH A SWIVELING HEAD AND A TORQUE LIMITER

(71) Applicant: CAIRDAC, Antony (FR)

(72) Inventors: Willy Regnier, Longjumeau (FR); An Nguyen-Dinh, La Riche (FR)

(73) Assignee: CAIRDAC, Antony (FR)

( * ) Notice: Subject to any disclaimer, the term of this patent is extended or adjusted under 35 U.S.C. 154(b) by 138 days.

(21) Appl. No.: 16/533,782

(22) Filed: Aug. 7, 2019

(65) Prior Publication Data
US 2020/0094048 A1 Mar. 26, 2020

(30) Foreign Application Priority Data
Sep. 25, 2018 (FR) ...................................... 1871085

(51) Int. Cl.
*A61N 1/05* (2006.01)
*A61N 1/375* (2006.01)
*A61N 1/378* (2006.01)

(52) U.S. Cl.
CPC ............. *A61N 1/059* (2013.01); *A61N 1/378* (2013.01); *A61N 1/3754* (2013.01); *A61N 1/3756* (2013.01)

(58) Field of Classification Search
CPC .... A61N 1/059; A61N 1/3754; A61N 1/3756; A61N 1/378; A61N 1/37518; A61N 1/37205; A61N 1/0573; A61B 5/283; A61B 5/6869; A61B 5/6861; A61B 5/6882; A61B 2560/0468; A61B 2562/162
See application file for complete search history.

(56) References Cited

U.S. PATENT DOCUMENTS

| | | | |
|---|---|---|---|
| 9,974,948 B2 | 5/2018 | Ollivier | |
| 2010/0274338 A1* | 10/2010 | Ollivier | A61N 1/0573 607/127 |
| 2012/0172892 A1 | 7/2012 | Grubac et al. | |
| 2012/0330392 A1* | 12/2012 | Regnier | A61N 1/3752 607/119 |
| 2014/0378991 A1 | 12/2014 | Ollivier | |
| 2014/0378992 A1* | 12/2014 | Ollivier | A61N 1/372 606/129 |

(Continued)

*Primary Examiner* — Gary Jackson
*Assistant Examiner* — Alexander M Eisenberg
(74) *Attorney, Agent, or Firm* — Steven M. Greenberg, Esq.; Shutts & Bowen LLP

(57) ABSTRACT

The capsule includes a tubular body and a front-end unit including an anchoring member for the anchoring of the capsule to a wall of a patient's organ. The front-end unit is mobile in relative axial rotation with respect to the tubular body, and a disengageable coupling member is adapted to allow this relative rotation when the tubular body receives an external rotational stress, the anchoring member then exerting a reaction torque higher than a predetermined threshold torque, and to prevent the relative rotation in the absence of external rotational stress applied to the tubular body. The coupling member may in particular include, between the front-end unit and the tubular body, a friction interface, with an elastically deformable element applying an axial compression between a bearing face of the tubular body and a support ring integral with the anchoring member.

14 Claims, 5 Drawing Sheets

(56) References Cited

U.S. PATENT DOCUMENTS

| | | | |
|---|---|---|---|
| 2015/0165189 A1* | 6/2015 | Ollivier | A61N 1/3756 607/127 |
| 2015/0374976 A1 | 12/2015 | Regnier et al. | |
| 2016/0296761 A1* | 10/2016 | Doan | A61N 1/057 |
| 2017/0106185 A1* | 4/2017 | Orts | A61N 1/0573 |
| 2017/0151429 A1* | 6/2017 | Regnier | A61N 1/3756 |

* cited by examiner

AUTONOMOUS IMPLANTABLE CARDIAC CAPSULE WITH A SWIVELING HEAD AND A TORQUE LIMITER

CROSS REFERENCE TO RELATED APPLICATIONS

This application claims priority under 35 U.S.C. § 119(a) to French patent application 1871085 filed on Sep. 25, 2018, the entire teachings of which are incorporated herein by reference.

BACKGROUND OF THE INVENTION

Field of the Invention

The present invention relates to implantable medical devices, in particular devices of the autonomous implantable capsule type. More particularly, the invention relates to such devices which are in the form of an autonomous capsule implanted in a heart chamber (ventricle, atrium or even arterial left heart chamber), hereinafter referred to as "autonomous capsule", "leadless capsule" or simply "capsule")

Description of the Related Art

Autonomous capsules are devoid of any physical connection to a main device, whether the latter is an implanted device (such as a stimulation pulse generator box) or a non-implanted device (external peripheral such as a programmer or a monitoring device for the remote follow-up of the patient), and are, for that reason, referred to as "leadless" capsules, to distinguish them from the electrodes or the sensors arranged at the distal end of a conventional lead, along the whole length of which run one or several conductors galvanically connecting the electrode or the sensor to a generator connected to an opposite, proximal end of the lead. In this case of cardiac application, the capsule continuously monitors the patient's rhythm and, if necessary, delivers to the heart pacing, resynchronization and/or defibrillation electrical pulses in case of rhythm disorders detected by the capsule. The capsule may be an epicardial capsule, fixed to the external wall of the heart, or an endocavitary capsule, fixed to the internal wall of a ventricular or atrial chamber, or also a capsule fixed to a vessel wall near the myocardium.

The capsules include various electronic circuits, sensors, etc., as well as wireless communication transmitter/receiver means for remote exchange of data, the whole being integrated in a body of very small size able to be implanted in sites of difficult access or leaving small room, such as the ventricle apex, the internal wall of the atrium, etc. United States Patent Application Publication No. 2009/0171408 A1 by Solem), United States Patent Application Publication No. 2015/374976 A1 by Regnier, United States Patent Application Publication No. 2017/0151429 A1 also by Regnier and Patent Cooperation Treaty Request Publication WO 2018/122244 A1 also by Regnier, each describe various examples of such intracardiac leadless capsules.

Capsules may be implanted in situ when provided, at a distal end, with an anchoring member adapted to enter the tissues of a body wall at the chosen implantation site. A typical example of such an anchoring member includes a protruding helical screw axially extending the capsule body and intended to enter the heart tissue by being screwed thereinto at the implantation site. This anchoring mode is however not limitative of the invention, which may also apply to other types of anchoring members, implementing, for example, tines, hooks, barbs, etc., entering the tissues to permanently secure the medical device thereto.

In the case of endocavitary capsules (i.e. capsules to be fixed to the inner wall of a ventricular or atrial chamber, by opposition to epicardial capsules, fixed to the outer wall of the heart), the "delivery", i.e. the positioning to the implantation site, consists in mounting the capsule at the end of a guide catheter of an implantation accessory, then to make it move along the peripheral venous network and to orientate it up to the chosen site, for example the apex of the right ventricular chamber. Once the implantation site reached, the practitioner imparts to the capsule, through the guide catheter, combined movements of axial translation (to make the capsule move forward then to exert a pressure against the heart wall) and of rotation of the capsule about itself (to operate the screwing of the anchoring member into the thickness of the heart wall). Once the capsule firmly anchored in the heart wall, the operator proceeds to the "release" of the capsule, i.e. its separation from the implantation accessory, so that the capsule then become fully autonomous.

One of the difficulties is, at the time of fixing the capsule into the wall, to avoid any risk of coring of the tissues due to an excessive screwing. For that purpose, it is imperative, at the time of screwing the anchoring member, not to exceed a limit torque (hereinafter "coring torque") beyond which the anchoring screw would be liable to locally tear the tissues under the effect of a rotation of the screw without forward move of the latter, until causing a laceration of the tissues and, in the extreme, a perforation of the wall with a risk of tamponade (in particular, in the case of an implantation into a thin wall such as the interatrial septum or the apical area of the right ventricle).

Patent Cooperation Treaty Request Publication WO 2017/202724 A1 by Ollivier, United States Patent Application Publication No. 2014/378991 A1 also by Ollivier and United States Patent Application Publication No. 2014/378992 A1 and U.S. Pat. No. 9,974,948 B2 to Ollivier, each disclose a solution implementing a specific unit combining a capsule and an implantation accessory. More precisely, the distal end of the guide catheter of the implantation accessory, on the one hand, and the proximal region of the capsule (that which is opposite to the anchoring member), on the other hand, are provided with cooperating translational and rotational fastening means, which can be disconnected from each other to release the capsule once the latter in position, and which are provided with a simple disengageable mechanism making it possible, during the screwing of the anchoring member, to limit the torque applied to the capsule by the implantation tool.

This mechanism consists of a helical spring used in radial compression (i.e. for its constriction effect), placed at the end of the guide catheter and rolled around a docking rod of the capsule at the distal portion of the latter. The spring then plays a double role of disengageable connection means and of torque limiter against an excessive screwing action that could lead to a coring of the tissues. The practitioner can hence continue to rotate the guide catheter without risk, because the additional torque occurring due to the reaction of the screw anchored into the tissues will be absorbed by the connection between the spring and the docking rod of the capsule, in the distal portion of the latter.

This solution, although it is efficient, has nevertheless for drawback to require an implantation accessory specifically adapted to the capsule, because the torque limitation function is located at the interface between the capsule and the implantation accessory. It hence cannot be implemented with standard implantation devices at the disposal of the practitioners, which limits its acceptance by these latter. An additional drawback of this known technique is the necessity to provide at the distal portion of the capsule (i.e. on the free end side, which is opposite the anchoring screw) a docking rod that is long enough to be able to be caught by the spring of the implantation tool. This requirement necessarily increases the overall length of the capsule, which goes against the requirements of extreme miniaturization imposed to leadless capsules.

BRIEF SUMMARY OF THE INVENTION

One of the objects of the invention is to propose a solution to this difficulty, thanks to a torque limitation system that is intrinsic to the capsule, hence allowing the delivery of the latter independently of the implantation accessory used by the practitioner.

Another object of the invention is to propose such a capsule, whose body rotational position with respect to the wall can possibly be modified after implantation, i.e. a capsule providing a possibility of rotation of the cylindrical body about its axis without causing at the same time a screwing/unscrewing movement of the anchoring member.

Still another object of the invention is to propose such a capsule, whose manufacturing cost is reduced, in particular thanks to a reduced number of parts and to the use of technologies and components that are field proven in similar applications.

More precisely, the invention proposes an autonomous implantable capsule including, a tubular body housing a set of functional elements of the capsule and, at a proximal end of the capsule, a front-end unit including an anchoring member for the anchoring of the capsule to a wall of a patient's organ. Characteristically of the invention, the front-end unit is, along with the anchoring member, mobile in relative axial rotation with respect to the tubular body, and the capsule further includes, between the front-end unit and the tubular body, a disengageable coupling member adapted to allow the relative rotation when the tubular body receives an external rotational stress that is applied thereto with the anchoring member anchored into the wall of the patient's organ, the anchoring member then exerting a reaction torque higher than a predetermined threshold torque, and preventing the relative rotation in the absence of external rotational stress applied to the tubular body.

In a first embodiment of the invention, the disengageable coupling member includes at least one friction interface between the front-end unit and the tubular body, and an elastically deformable element adapted to apply an axial compression force between a first bearing face, rotationally integral with the tubular body, and a second bearing face, rotationally integral with the front-end unit.

Preferably, in the absence of external rotational stress applied to the tubular body, the elastically deformable element applies, at the friction interface, a force higher than the predetermined threshold torque.

Also, preferably, the disengageable coupling member includes a support ring rotationally integral with the anchoring member and coming into frictional bearing against a front annular surface of the tubular body, located at the proximal end of the latter.

In this latter case, the elastically deformable element can apply the axial compression force against the support ring towards the front annular surface, and the support ring can include two faces, including a first face directed towards the front annular surface, with a rotational degree of freedom and a first frictional contact at the interface between the first face and the front annular surface, and a second, opposite face, directed towards the elastically deformable element, with a rotational degree of freedom and a second frictional contact at the interface between the second face and the elastically deformable element.

In this first embodiment, the tubular body and the front-end unit are not mobile in axial translation between each other.

In a second embodiment of the invention, the disengageable coupling member includes a support ring rotationally integral with the anchoring member, a front surface of the tubular body, located at the proximal end of the latter, opposite the support ring, and conjugated shapes provided on the support ring and on the front surface, respectively, the conjugated shapes allowing a mutual fitting of the tubular body with the front-end unit to allow the support ring, and correlatively the anchorage member integral with the latter, to be rotated by the fitting member of the front surface under the effect of the external rotational stress applied to the tubular body.

In this second embodiment, the tubular body and the front-end unit can be mobile in axial translation relative to each other, and the tubular body can carry, at its proximal end, an element intended to bear against the wall of the patient's organ, this element being adapted to exert, during the penetration of the anchoring member, an axial reaction force capable of axially disconnecting the respective conjugated shapes of the support ring and of the front surface.

Advantageously, the disengageable coupling member includes an elastically deformable element adapted to axially stress the conjugated shapes towards each other, in particular an elastically deformable element adapted to undergo, under the effect of the axial reaction force, a deformation from a non-deformed state to a maximum deformation state corresponding to the predetermined threshold torque; this elastically deformable element can in particular be an element of the group consisted of: corrugated ring, compression spring, leaf spring, deformable plastic ring and flexible material spacer.

In a third embodiment of the invention, the tubular body and the front-end unit are not mobile in axial translation relative to each other, and the disengageable coupling member includes an elastically deformable element adapted to undergo, under the effect of the reaction torque, a deformation between: a state in which the elastically deformable element exerts between the conjugated shapes a radial constriction force causing the mutual fitting of the tubular body with the front-end unit, and a maximum deformation state likely to disconnect the tubular body and the front-end unit, for a reaction torque corresponding to the predetermined threshold torque.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
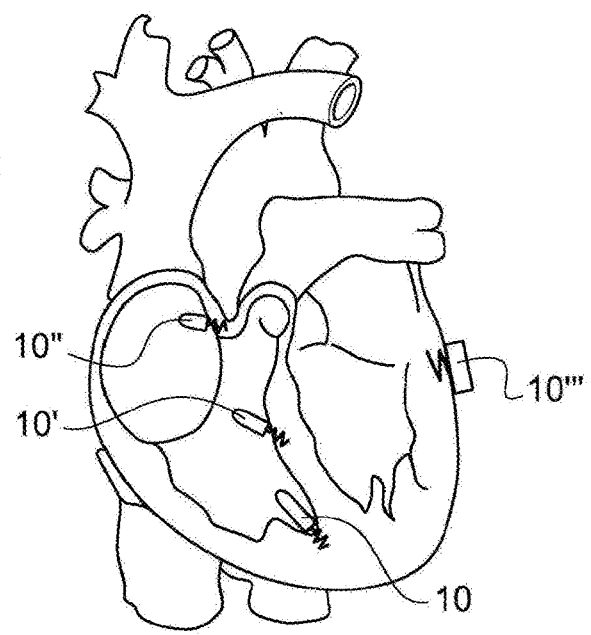
FIG. 1 illustrates medical devices of the leadless capsule type in their environment, with various examples of implantation sites in, on or near the heart of a patient.

In FIG. 1 are shown various possibilities of implantation sites for a device of the leadless type, in an application to cardiac pacing. Hence, the capsule 10 is implanted inside a myocardium chamber (endocavitary implant), for example at the apex of the right ventricle. As a variant, the capsule may also be implanted on the right interventricular septum, as in 10', or on an atrial wall, as in 10". The device may also be an epicardial capsule placed in an external region of the myocardium, as in 10"'.

In each case, the leadless capsule is fixed to the heart wall by means of a protruding anchoring system such as a helical screw entering the heart tissue for holding it to the implantation site. Other anchoring systems can be used, and do not modify in any way the implementation of the present invention.

Figure 2:
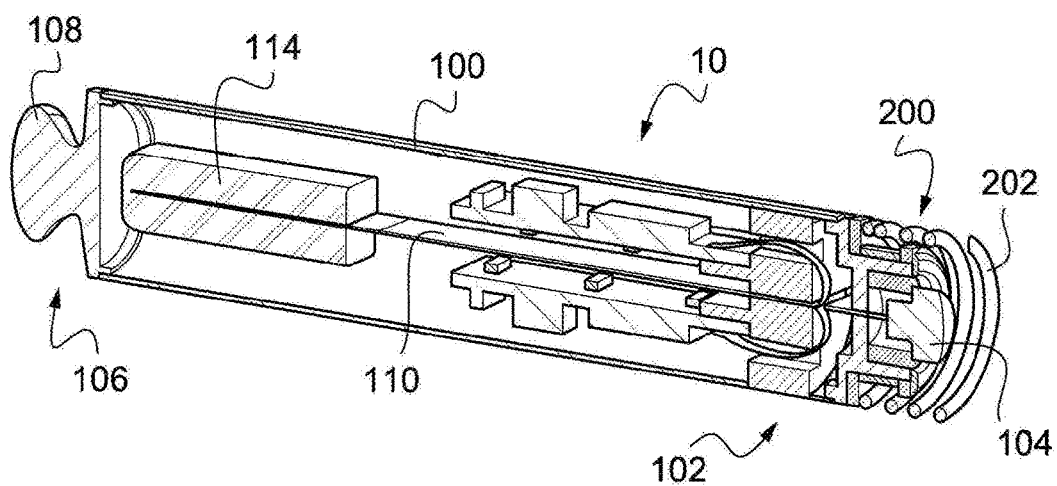
FIG. 2 is a longitudinal cross-sectional perspective view of an example of leadless capsule, showing the mechanical configuration of the different elements located inside the tubular envelope of the capsule.

FIG. 2 is a longitudinal cross-sectional perspective view of an example of leadless capsule showing the mechanical configuration of the different elements located inside the tubular envelope of the capsule.

The capsule 10 is in the external form of an implant with a body including a cylindrical elongated tubular body 100 enclosing the various electronic and power supply circuits of the capsule as well as, in the illustrated (non-limitative) example, an energy harvester with a pendular unit. The typical dimensions of such a capsule are a diameter of the order of 6 mm for a length of about 25 40 mm.

The elongated tubular body 100 is closed at its front (proximal) end 102 by a front-end unit 200 carrying a helical screw 202 for the anchoring of the capsule to a wall of a heart chamber, as illustrated hereinabove with respect to FIG. 1 (this anchoring mode being of course not in any way limitative). A sensing/pacing electrode 104, in contact with the heart tissue at the implantation site, collects the cardiac depolarization potential and/or applies pacing pulses.

The opposite, rear (distal) end 106 of the tubular body 100 of the capsule 10 has an atraumatic rounded shape and is provided with suitable means 108, such as a gripping shape for the connection to a guide catheter or another implantation accessory usable at the time of implantation or explanation of the capsule. These means allow the practitioner, by a controlled action of combined rotation and translation of the guide catheter, to guide the capsule towards the implantation site and to secure it thereto by screwing the anchoring element into the wall.

The capsule 10 is advantageously provided with an energy harvesting module including an inertial pendular unit that oscillates, inside the capsule, following the various external stresses to which the capsule is subjected, and which can in particular result from the movements of the wall to which the capsule is anchored, which are transmitted to the implant by the anchoring screw 202, and/or the blood flow rate variations in the medium surrounding the implant, which produce oscillations of the implant at the rhythm of the heartbeats, and/or the various vibrations transmitted by the heart tissues.

The pendular unit may in particular consist of a piezoelectric beam 110 clamped at one of its ends, and whose opposite, free end is coupled to a mobile inertial mass 114. The piezoelectric beam 110 is an elastically deformable flexible beam that constitutes, with the inertial mass 114, a pendular system or the mass-spring type that, due to the inertia of the inertial mass 114, subjects the beam 110 to a deformation of the vibratory type on either side of a neutral or non-deformed position corresponding to its stable rest position in the absence of any stress. The piezoelectric beam 110 further performs a function of mechanical-electrical transducer for converting the mechanical stress applied to it when it is bent into electrical charges that are then collected to produce an electrical signal that, after being rectified, stabilized and filtered, will power the various electronic circuits of the capsule.

Figure 3:
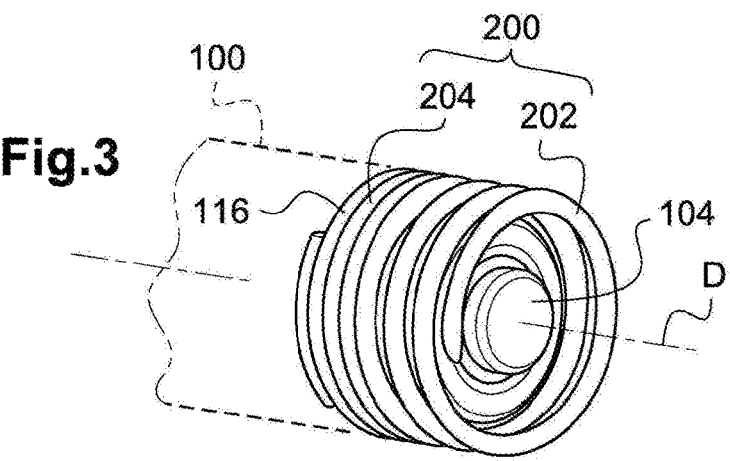
FIG. 3 is a perspective overall view of the front-end unit according to the invention, located at the proximal end of a capsule such as that of FIG. 2.

FIG. 3 illustrates, in isolation, the front-end unit 200 of the capsule mounted at the proximal end of the tubular body 100 of the capsule, with the electrode 104 intended to bear against the surface of the tissue at the implantation site and the helical screw 202 intended to enter this tissue for the anchoring of the capsule to the implantation site.

The screw 202 is rotationally integral with a support ring 204, the screw being for example welded to this support ring, the two elements being metallic, for example made of stainless steel, such as 316L steel or also a metal such as titanium, tantalum or a nickel-titanium alloy of the nitinol type.

(It will be noted by the way that all the elements integral with the tubular body 100 will be denoted by a numerical reference of the type 1nn, whereas all those which are integral with the front-end unit 200 will be denoted by a numerical reference of the type 2nn).

The tubular body 100 is ended, opposite the support ring 204, by a closing cap 116 of substantially flat shape and against which bears the support ring 204. The closing cap 116, just as the tubular body 100 of the capsule, are metallic element, for example made of titanium or stainless steel, such as 316L steel, or also a nickel-titanium alloy of the nitinol type, both parts 100 and 116 being for example welded to each other.

Characteristically of the invention, the front-end unit 200, hence including the anchoring screw 202 with its support ring 204, has, with respect to the tubular body 100 and the closing cap 116 thereof, an axial rotational degree of freedom (i.e. about central axis D).

In certain particular configurations, such as those of the embodiments of FIGS. 6 and 7 that will be described hereinafter, the front-end unit 200 and the tubular body 100 can also have an axial translational degree of freedom (i.e. parallel to axis D). On the other hand, in other embodiments, such as those illustrated in FIGS. 4 and 11, the front-end unit 200 has only one axial rotational degree of freedom with respect to the tubular body 100 and to the elements that are integral with the latter.

Also characteristically of the invention, the tubular body 100 as well as the elements with which it is integral, on the one hand, and the front-end unit 200, on the other hand, are coupled to each other by disengageable means, thanks to various mechanisms several embodiments of which will be described with reference to FIGS. 4 to 12. These disengageable means are in particular adapted to perform a function of torque limiter between the tubular body (that receives an external stress at the time of implantation via the implantation tool handled by the practitioner) and the anchoring screw (that enters the tissue, and for which it is essential to avoid any coring effect).

The torque limiter mechanism makes it possible, when the tubular body is rotationally stressed and hence applies to the anchoring screw a corresponding torque that allows the latter to enter the tissue for the transmission of this driving torque as long as the latter is lower than a predetermined threshold torque (chosen to be lower than the coring torque) and, if the driving torque exceeds this threshold, prevents the coring, either by limiting this torque (which will continue to be transmitted from the tubular body to the front-end unit), or by fully disengaging the front-end unit of the tubular body (hence ending the transmission of the driving torque). The predetermined threshold torque triggering the disconnection of the front-end unit from the tubular body is typically lower than 1 N·cm, to avoid any risk of coring by the helical screw at the time of implantation. Concretely, the reaction torque increases relatively suddenly when the front face of the capsule (herein the electrode 104) touches the surface of the heart tissue, then exerting to the anchoring screw an axial reaction force which, in the absence of disengagement action or torque limitation, would be liable to produce a coring.

It will also be seen that the various disengageable coupling mechanisms described make it possible, once the disengagement operated, to keep a rotational degree of freedom of the tubular body with respect to the front-end unit, so that the direction of the tubular body can possibly be modified in situ without changing the position of the helical screw, hence by keeping the anchoring as it was initially made.

This subsequent modification of the angular direction will result from a rotary action exerted on the tubular body, it being understood that, in the absence of such a stress, the direction of the capsule will not be modified and will remain that which had been obtained initially.

First Embodiment of the Invention

Figure 4:
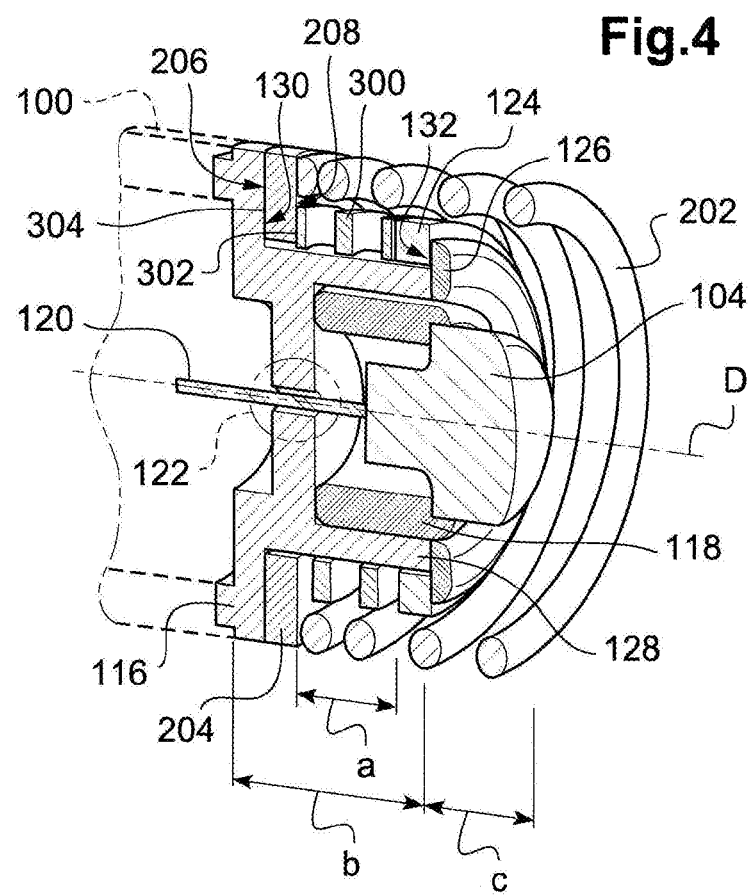
FIG. 4 is a cross-sectional perspective view of a first embodiment of a front-end unit of a capsule according to the invention.
Figure 5:
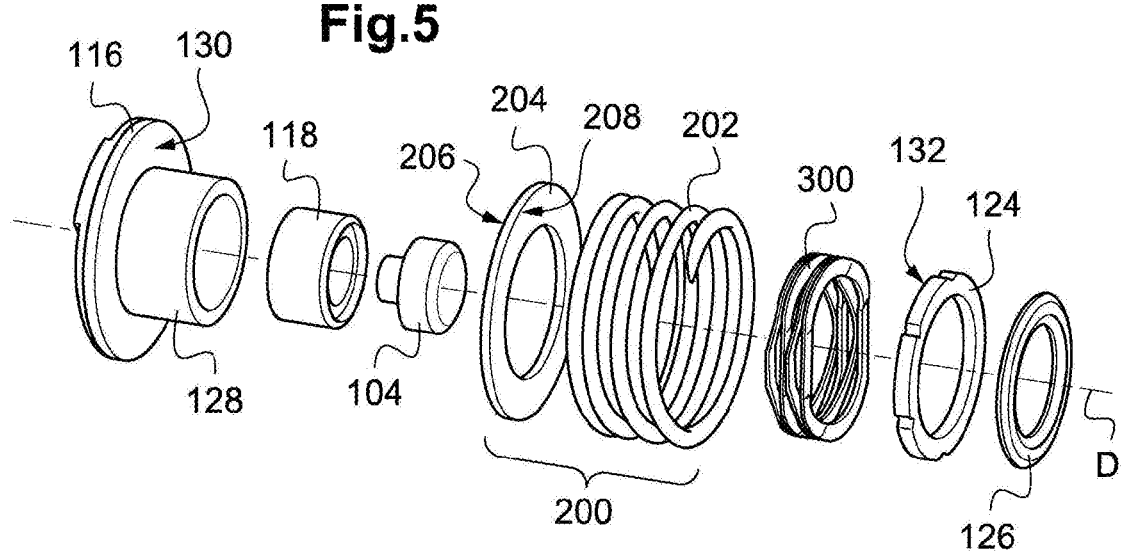
FIG. 5 is an exploded perspective view of the different elements constituting the unit of FIG. 4.

A first embodiment of the invention, in which the front-end unit 200 and the tubular body 100 are mobile relative to each other with a single, rotational degree of freedom, about axis D, will now be described with reference to FIGS. 4 and 5.

The tubular body 100 and its closing cap 116 form a unit integral with the electrode 104 carried by an electrode support ring 118 made of an electrically isolating material, for example a polyurethane thermoplastic polymer of the Tecothane¬Æ type or a polymer of the PET (polyethylene terephthalate) or PEEK (polyetheretherketone) type, or another injectable plastic material. The electrode 104 is connected to the electronic circuits located inside the tubular body 100 by a connection wire 120 passing through the cap 116 and isolated from the latter by a feedthrough 122 (illustrated in more detail in FIGS. 7 and 11).

The cap 116 includes a tubular protrusion 128 receiving and supporting a ring-shaped tip 124 with, advantageously, in the region close to the electrode 104 an additional ring 126 incorporating a material liable to diffuse a steroid agent.

As regards the front-end unit 200, which is mobile in rotation with respect to the just-described various elements 100 to 128, this unit includes the support ring 204, which is integral with the anchoring screw 202 and includes a bearing surface 206 directed towards an annular counterpart surface 130 of the cap 116. These two surfaces 130 and 206, which are both metallic, form a first interface 304 with a mutual friction effect.

The opposite surface 208 of the support ring 204 bears against an annular spring 300, the spring 300 and the ring 204 being not integral with each other. Between the two elements composed of the surface 208 of the ring 204 and the spring 300 is formed a second interface 304 with a mutual friction effect. On the proximal side, the spring 300 bears against a surface 132 of the cap 124.

The annular spring 300, which is hence axially caught between the support ring 204 and the cap 124, exerts to the support ring 204 an axial force towards the tubular body 100, this force resulting in a friction effect at the interfaces 302 and 304.

This friction coupling mechanism between, on the one hand, the tubular body 100 and the different elements that are integral therewith and, on the other hand, the front-end unit 200 with, in particular, the anchoring screw 202, makes it possible to limit the torque transmitted by the tubular body to the anchoring screw 202 and to hence exert the desired anti-coring torque limiter effect.

It will also be noted that it is still possible to axially redirect the tubular body once the capsule anchored into the wall, without exerting a rotary action to the screw, hence without risk of over-screwing liable cause a coring.

This faculty may turn out to be interesting in the case of a capsule provided with an energy harvester such as that illustrated in FIG. 2, including an inertial mass mounted a the end of a flexible beam: with this configuration, the energy harvesting may vary as a function of the beam bending direction in space with respect to the heart wall, so that it may be advantageous to try to optimize the energy conversion by rotating the capsule body up to find the position that maximizes this conversion.

Moreover, if it is desired to explant the capsule, a rotation torque exerted in the reverse direction on the tubular body will allow transmitting the unscrewing movement to the helical screw and hence progressively detaching the capsule from the wall.

For the spring 300, the choice of a corrugated spring has for advantage a very high compactness, which is compatible with the requirements of extreme miniaturization of the leadless capsules. The spring length, i.e. the interval included between the opposite surfaces 208 and 132, is typically of the order of a=1.6 mm, which allows making a unit of reduced length, for example of length b=3 mm (the protruding portion of the screw, corresponding to the length entering the wall, being typically of about c=1.6 mm).

The advantage of the corrugated spring is the axial space saving allowed, typically 50% with respect to a conventional helical wire spring. Other types of springs or elements of similar operation can however be contemplated, such as: spacer made of flexible material, for example silicon, helical compression spring, leaf spring, deformable plastic ring, etc., the important being that this element can generate a sufficient friction to limit the torque to the chosen value, while maintaining the angular direction of the tubular body 100 with respect to the front-end unit in the absence of torque applied from the outside of the tubular body.

Second Embodiment of the Invention

Figure 6:
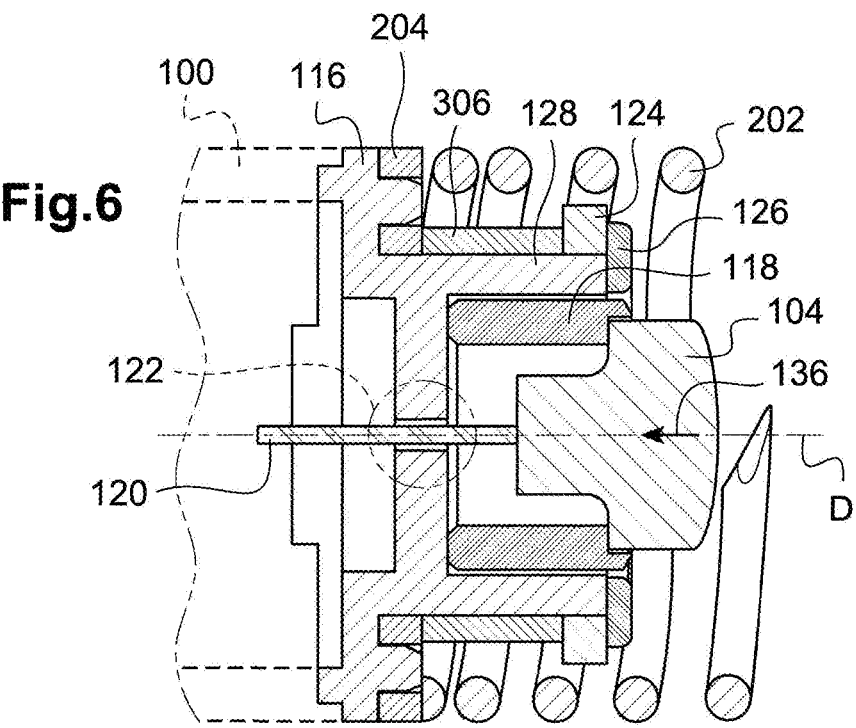
FIG. 6 is a cross-sectional view of a second embodiment of a front-end unit of a capsule according to the invention.

FIG. 6 illustrates a second embodiment of the invention, in which the tubular body 100 and the front-end unit 200 are not only rotationally mobile about axis D, but also mobile in axial translation: more precisely, the unit formed by the tubular body 100 with the elements it carries, in particular the electrode 104, can move backward in the distal direction (i.e. towards the left with the conventions of the figure) with respect to the front-end unit 200. Before this axial translation move, the two units 100 and 200 are rotationally integral with each other, but once the axial translation performed, they become rotationally free from each other.

The axial translation occurs when, at the time of screwing, the front face of the electrode 104 comes into contact with the surface of the tissue which the screw 202 is entering. The electrode 104 and hence the tubular body 100 can no longer move forward, whereas, due to the rotation, the anchoring screw 202 continues entering the tissue. It results therefrom a progressive axial backward move (arrow 136) of the tubular body 100 and the electrode 104 with respect to the front-end unit 200 and the screw 202, up to producing a disengagement of these two units with respect to each other.

Figure 8:
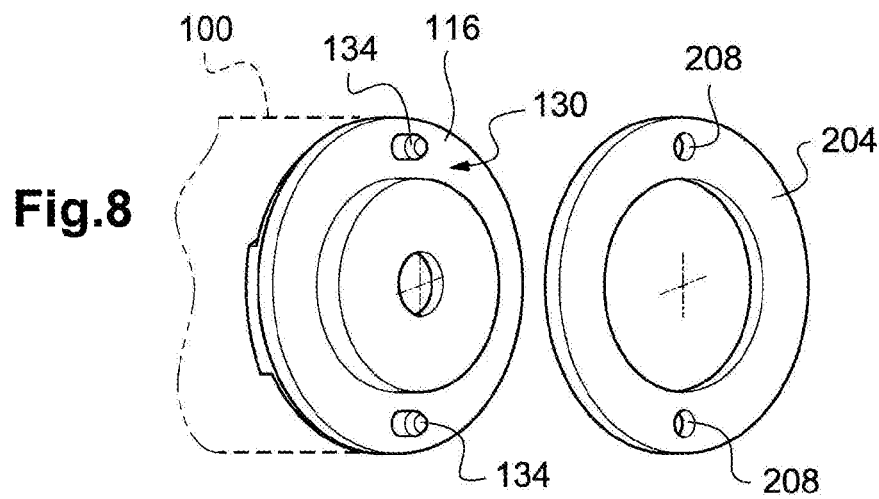
FIG. 8 shows, in isolation, the front metal cap of the capsule and the conjugated support ring integral with the anchoring screw, for the embodiment of FIG. 6.

For that purpose, as illustrated in FIG. 8, the face 130 of the cap 116 directed towards the support ring is provided with pins 134 intended to fit into counterpart bores 208 of the support ring 204. Moreover, an elastic element 306 (FIG. 6), for example a silicon ring, is interposed between the cap 124 and the support ring 204, so as to exert an axial force of a predetermined level between the face 130 of the cap 116 and the support ring 204.

That way, the progressive entering of the screw 202 through the tissue, which has for effect to axially push back the electrode 104 and hence the tubular body 100 and its closing cap 116 (arrow 136), will have for effect to progressively get the pins 134 out of the bores 208. When the pins will be fully out of the bores, then the support ring 205 will be rotationally disconnected from the cap 116, which performs the desired torque limitation function.

Figure 9:
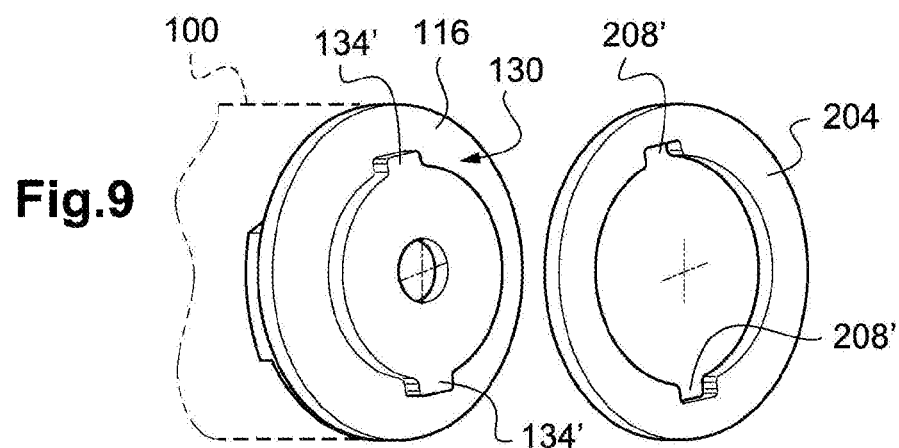
FIG. 9 illustrates a first variant of the two elements of FIG. 8.
Figure 10:
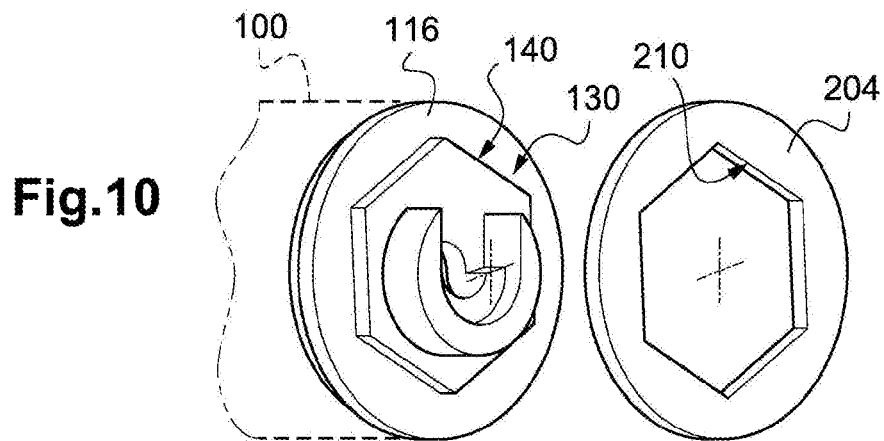
FIG. 10 illustrates a second variant of the two elements of FIG. 8.

FIGS. 9 and 10 illustrate variants of FIG. 8, in which the pins 134 and the bores 208 are replaced by protrusions 134' cooperating with counterpart notches 208' of the support ring 204 or (FIG. 10) by a non-circular profile 140 (hexagonal in the illustrated example) cooperating with a conjugated profile 210 of the support ring 204.

Figure 7:
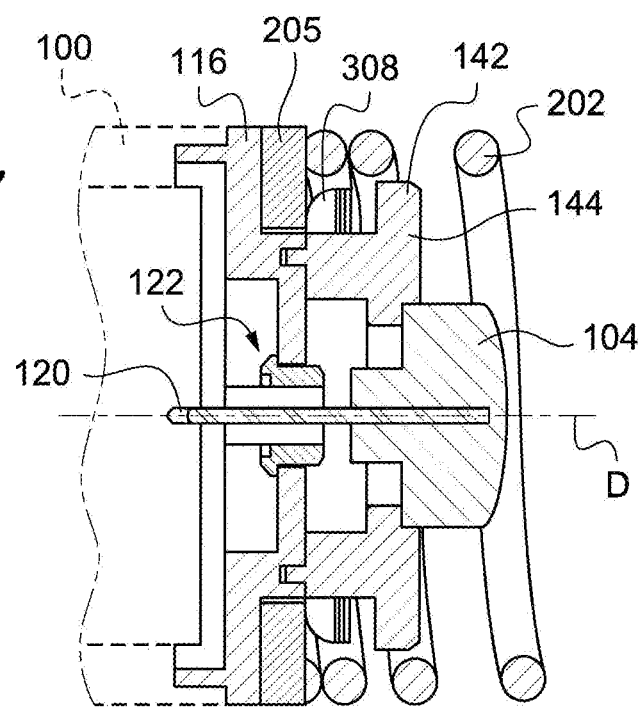
FIG. 7 is a cross-sectional view of a variant of the embodiment illustrated in FIG. 6.

FIG. 7 illustrates a variant of an embodiment of FIG. 6. This variant implements as an elastic element corrugated rings 308 interposed between the support ring 205 and a shoulder 142 of an annular element 144 integral with the cap 116.

The progressive penetration of screw 202 has for effect to push back the electrode 104 and the tubular body 100 in the distal direction (towards the left with the conventions of the figure), whereas the screw 202 will continue to progress into the tissue, in proximal direction (towards the right). This relative translation move has for consequence to compress the corrugated rings 308, up to causing a disengagement between the closing cap 116 and the support ring 204.

Third Embodiment of the Invention

Figure 11:
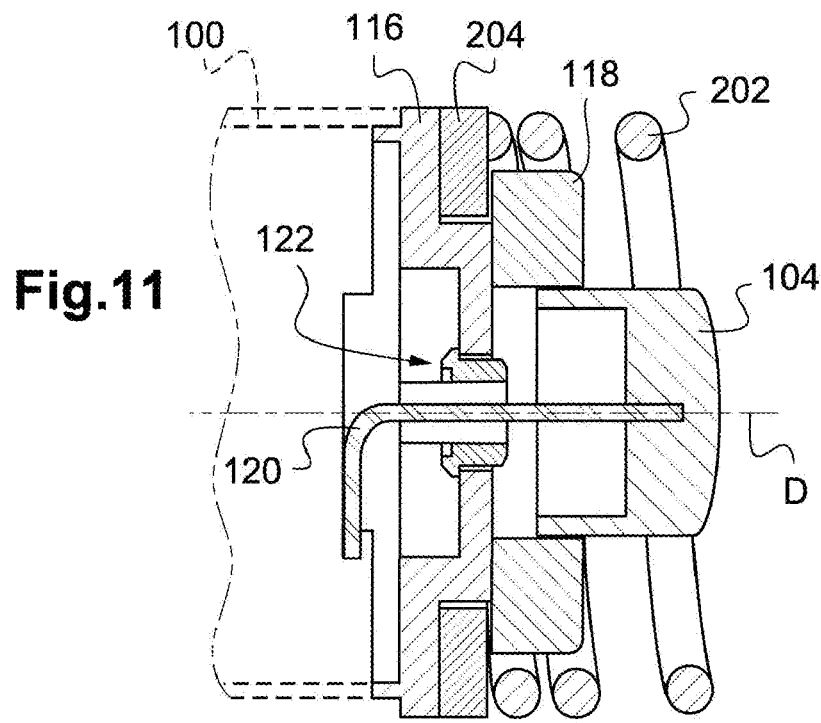
FIG. 11 illustrates a third embodiment of a front-end unit of a capsule according to the invention.

FIG. 11 illustrates a third embodiment of the invention, in which the tubular body 100 and the electrode 104, on the one hand, and the front-end unit 200 with the anchoring screw 202, on the other hand, are not axially mobile, unlike the previous embodiment.

Figure 12:
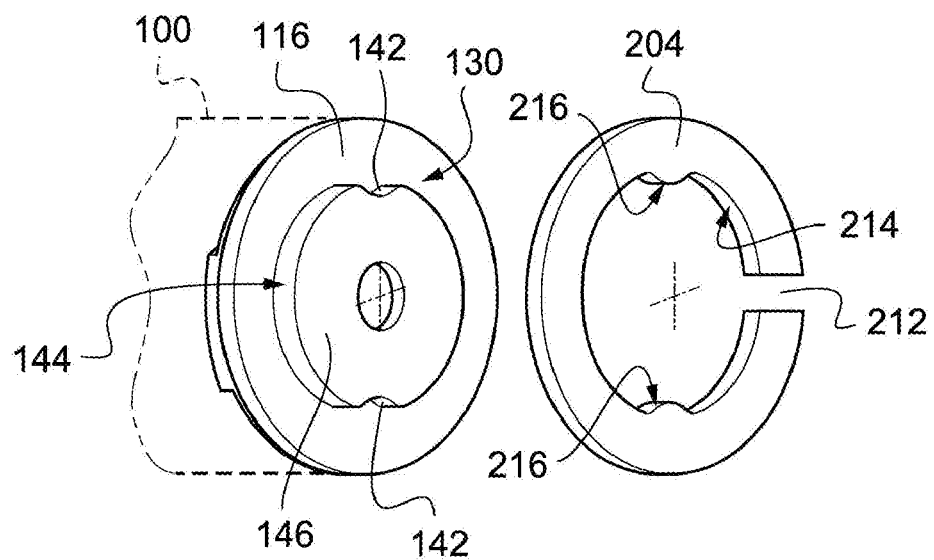
FIG. 12 illustrates two conjugated elements used by the front-end unit of FIG. 11.

In this third embodiment, the elastic element is composed of the support ring 204 itself that, as can be seen in FIG. 12 in which it is illustrated in isolation, is a split annular ring, with a radial slot 212. This radial slot provides this support ring 204 with radial elasticity, like an elastic ring of the circlip type.

The support ring 204 is moreover provided, at its inner periphery 214, with protrusions 216 cooperating with counterpart recesses 142 provided on a ramp external surface 144 of a shoulder 146 of the closing cap 116.

As long as the torque exerted on the tubular body 100, and hence the torque transmitted to the cap 116 and to the support ring 204, via the conjugated elements 142, 216, is lower than a predetermined torque, the support ring 204 is not deformed, which allows the transmission of this rotation torque to the support ring 204 and hence to the screw 202. On the other hand, when the torque increases beyond the prescribed value, the split support ring 204 is radially deformed, so that the protrusions 216 go out of the recesses 142, hence performing the desired torque limitation and disengagement function.

Of note, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", and/or "including," when used in this specification, specify the presence of stated features, integers, steps, operations, elements, and/or components, but do not preclude the presence or addition of one or more other features, integers, steps, operations, elements, components, and/or groups thereof.

As well, the corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

1. An implantable autonomous capsule, comprising:
    a tubular body housing a set of functional components of the capsule, and
    at a proximal front end of the capsule, a front-end unit comprising an anchoring member for the anchoring of the capsule to a wall of a patient's organ, and
    at a distal, free-end side of the capsule, means for connecting the capsule to an implantation accessory,
    wherein the front-end unit is, along with the anchoring member, mobile in relative axial rotation with respect to the tubular body,
    and wherein the capsule further comprises, at said proximal, front-end of the capsule, between the front-end unit and the tubular body:
    a disengageable coupling member comprising a torque limiter adapted to:
        allow said relative rotation when the tubular body receives from the distal, free-end side of the capsule an external rotational stress that is applied thereto with the anchoring member anchored at the proximal end of the capsule into the wall of the patient's organ, the anchoring member then exerting a reaction torque higher than a predetermined threshold torque, and
        prevent said relative rotation in the absence of external rotational stress applied to the tubular body, and
    a support ring rotationally integral with the anchoring member.

2. The capsule of claim 1, wherein the disengageable coupling member comprises:
    at least one friction interface between the front-end unit and the tubular body; and
    an elastically deformable spring member adapted to apply an axial compression force between a first bearing face, rotationally integral with the tubular body, and a second bearing face, rotationally integral with the front-end unit.

3. The capsule of claim 2, wherein, in the absence of external rotational stress applied to the tubular body, the elastically deformable spring member applies, at the friction interface, a force higher than the predetermined threshold.

4. The capsule of claim 2, wherein the disengageable coupling member comes into frictional bearing against a front annular surface of the tubular body, located at a proximal end of the anchoring member.

5. The capsule of claim 4, wherein the elastically deformable spring member applies the axial compression force against the support ring towards the front annular surface.

6. The capsule of claim 4, wherein the support ring comprises two faces, comprising:
    a first face directed towards the front annular surface, with a rotational degree of freedom and a first frictional contact at an interface between the first face and the front annular surface; and
    a second, opposite face, directed towards the elastically deformable spring member, with a rotational degree of freedom and a second frictional contact at the interface between the second face and the elastically deformable spring member.

7. The capsule of claim 2, wherein the tubular body and the front-end unit are not mobile in axial translation between each other.

8. The capsule of claim 1, wherein the disengageable coupling member comprises:
    a front surface of the tubular body, located at the proximal end of the anchoring member, opposite the support ring; and
    conjugated shapes provided on the support ring and on the front surface, respectively, the conjugated shapes allowing a mutual fitting of the tubular body with the front-end unit to allow the support ring, and correlatively the anchoring member integral with the support ring, to be rotated by a fitting member of the front surface under the effect of the external rotational stress applied to the tubular body.

9. The capsule of claim 8, wherein the tubular body and the front-end unit are mobile in axial translation relative to each other, and the tubular body carries, at its proximal end, an electrode assembly intended to bear against the wall of the patient's organ, said electrode assembly being adapted to exert, during the penetration of the anchoring member, an axial reaction force capable of axially disconnecting the respective conjugated shapes of the support ring and of the front surface.

10. The capsule of claim 9, wherein the disengageable coupling member further comprises an elastically deformable spring member adapted to axially stress the conjugated shapes towards each other.

11. The capsule of claim 10, wherein the elastically deformable spring member is adapted to undergo, under the effect of said axial reaction force, a deformation from a non-deformed state to a maximum deformation state corresponding to said predetermined threshold torque.

12. The capsule of claim 2, wherein the elastically deformable spring member is one of: a corrugated ring, a compression spring, a leaf spring, a deformable plastic ring and a flexible material spacer.

13. The capsule of claim 10, wherein the elastically deformable spring member is one of: a corrugated ring, a compression spring, a leaf spring, a deformable plastic ring and a flexible material spacer.

14. The capsule of claim 8, wherein the tubular body and the front-end unit are not mobile in axial translation relative to each other, and the disengageable coupling member comprises an elastically deformable spring member adapted to undergo, under the effect of said reaction torque, a deformation between:
    a state in which the elastically deformable spring member exerts between the conjugated shapes a radial constriction force causing the mutual fitting of the tubular body with the front-end unit, and
    a maximum deformation state configured to disconnect the tubular body and the front-end unit, for a reaction torque corresponding to said predetermined threshold torque.

* * * * *